United States Patent [19]

Stein

[11] 4,264,492

[45] Apr. 28, 1981

[54] ENKEPHALIN-LIKE COMPOUNDS IN BOVINE ADRENAL MEDULLA

[75] Inventor: Stanley Stein, Bloomfield, N.J.

[73] Assignee: Hoffmann-La Roche Inc., Nutley, N.J.

[21] Appl. No.: 70,960

[22] Filed: Aug. 30, 1979

[51] Int. Cl.³ .................... C07C 103/52; A61K 37/02
[52] U.S. Cl. ............................ 260/112.5 R; 424/177
[58] Field of Search .................. 260/112.5 R; 424/177

[56] References Cited

PUBLICATIONS

M. Schultzberg, et al., Biological Abstr. 67, 40457 and 74902.
J. W. Holaday, et al., Biological Abstr. 65, 54489.
R. V. Lewis, et al., Biochem. and Biophys. Res. Commun. 89, (1979), pp. 822–829.

*Primary Examiner*—Delbert R. Phillips
*Attorney, Agent, or Firm*—Jon S. Saxe; George M. Gould; John B. Wilson

[57] ABSTRACT

Enkephalin-like compounds can be extracted from bovine adrenal glands, showing opiate agonist activity and immunoreactive with enkephalin antibodies.

1 Claim, No Drawings

ENKEPHALIN-LIKE COMPOUNDS IN BOVINE ADRENAL MEDULLA

BACKGROUND OF THE INVENTION

The present invention relates to compounds useful as analgesic agents. Particularly the compounds of this invention are enkephalin-like compounds. More particular, the invention compounds are structurally related to Met-enkephalin which has been characterized as an endogenous opioid peptide.

Peptides with opiate properties, in particularly the pentapeptides methionine enkephalin (Met-Ek) and (Leu-Ek), have been isolated from extracts of animal tissue and their amino acid sequences have been confirmed [Hughes, J. et al., Nature 258, 577 (1975)]; the biosynthetic pathway for these enkephalins, however, has not been established.

Furthermore, Met-EK and Leu-EK from mammolian brain produce a weak and short lined anagesia following intracerebraventricular or intravenous administration to mice [Buscher, H. H., et al. Nature 261, 423 (1976)] and rats [Belluggi, J. D., et al. Nature 260; 625 (1976)]. The short half life of the activity of the enkephalin may be due to rapid destruction by brain enzymes [N. Marks, et al., Biochem, Biophys. Res. Comm. 74, 1552 (1977)].

Synthetic enkephalin analogs in which $Gly^2$ has been replaced by D-Ala [Pert, C. B., et al. Science 194, 330 (1976)]; or $Leu^5$ [Baxter, M. G., et al. Proceed. Brit. Pharm. Soc. p. 455 (1977)] or derivating of enkephalin obtained by increased chain length as H-Tyr-Tyr-Gly-Gly-Phe-Leu-OH or H-Tyr-Gly-Gly-Phe-Leu-Leu-OH [Terenius, L. et al. Biochem, Biophys. Res. Comm. 73, 632 (1976)]. While U.S. Pat. No. 4,103,005 describes the synthesis and biological activity of enkephalin analogs, D-$Met^2$, $Thz^5$ and D-$Thr^2$, $Thz^5$-enkephalinamide show prolonged activity and an increased potency. There has been no showing however that these synthetic analogs or derivatives are endogenous opioid peptides.

Our studies to elucidate this enkephalin in biosynthetic pathway were initially centered on the striatum which contained large amounts of enkephalin. This tissue was difficult to work with and difficult to obtain in large quantities. We were thus forced to look for other tissues to work with. Immunocytochemical observations in the adrenal medulla [Schultzberg, M. et al., Neuroscience 3, 1169 (1978)] had shown the presence of relatively large amounts of enkephalin immunoreactive material. Others had shown the presence of enkephalins and possibly other opioid peptides in the adrenal gland. These preliminary studies indicated to us that the adrenal gland might be a suitable tissue in which to study the biosynthesis of the enkephalins. Utilizing high performance liquid chromatography (HPLC) and fluorometric detection we have analyzed the contents of bovine adrenal medullary chromaffin granules. In these granules we have shown the presence of high molecular weight proteins that can be cleaved with trypsin to yield peptides with opioid activity in both radioreceptor and radioimmunoassays. In addition to these large proteins we have found a number of smaller peptides some of which are active in their native form and others that yield active tryptic fragments. We have isolated several of these peptides and precursors and purified some of them to homogeneity.

DESCRIPTION OF THE INVENTION

The present invention relates to the isolation and purification of endogenous substances having enkephalin-like properties from bovine adrenal glands.

Chromatography of extracts of bovine adrenal medulla on Sephadex G-100 give five peaks of radioreceptor active material. Chromaffin granules from the bovine adrenal medulla were lysed and subjected to the same chromatography on Sephadex G-100. The same five peaks of activity were again observed. Peaks II and III have recently been purified and characterized.

Peak IV from the G-100 was chromatographed on an HPLC Lichrosorb RP-18 column. The results show a complex pattern of peptides with at least 6 peptides having opioid activity or yielding opioid active peptides after digestion with trypsin.

Further chromatography of each of these peaks using RP-18 or CN-propyl HPLC columns has resulted in an even more complex pattern of opioid peptides all of which except IV-B, show much greater activity after trypsin digestion.

The acid extract from chromaffin granules, after deproteinization by TCA corresponds to Peak V. In a separate investigation of these peptides of molecular weight less than 1,500, granules were isolated from 5 bovine adrenal medullae. The deproteinized acid extract from these granules was lyophilized. The residue was then dissolved in 0.5 M formic acid - 0.14 M pyridine pH 4.0 and applied to a HPLC RP-18 column. Fractions were collected and tested for opioid activity with the radioreceptor assay. Opioid activity was detected not only in the calibrated Met- and Leu-enkephalin regions, but also in two regions before the elution position of Met-enkephalin (fractions 6 and 7) and one region after the elution position of Leu-enkephalin (fraction 16).

This chromatographic pattern corresponds directly to that obtained from bovine striatal extracts although the relative amounts of these peptides differ. The elution times differ slightly in the two figures because of the direct application of the acid extracts (71 ml) and a slight change in gradient conditions. Most importantly, the relative positions of these unknown opioid peptides relative to Met- and Leu-enkephalins are identical.

In a typical isolation the enkephalin concentration in the lysed granule supernatant was 8.5 nmol/mg protein with the Metanalog comprising about 65% of the total. As much as 1.2 nmol of enkephalin was obtained from 1 g of adrenal medulla. Fractions designated as 6, 7 and 16 were present in concentrations of 0.4, 0.5 and 0.5 nmol/mg protein respectively. When protease inhibitors were not used during the isolation procedure, the yields are lower.

In order to determine whether fractions 6, 7 and 16 were indeed separate entities differing chromtographically from the enkephalins, these fractions were lyophilized, redissolved in 1 ml of 0.5 M formic acid 0.14 M pyridine (pH 4.0) and rechromatographed. Each opioid peptide eluded at its original position. Note that rechromatography of fraction 7 indicates some contamination of the sample by Met-enkephalin. Thus, there are opioid peptides in the chromaffin granules besides Met- or Leu-enkephalin.

METHODS AND CHARACTERIZATIONS

Bovine adrenal glands were obtained from a local slaughterhouse and stored on ice until used (2 hrs). The medullas were dissected out and chromaffin granules prepared by the procedure of Smith and Winkler [Biochem. J., 103, & 80 (1967)]. The isolated chromaffin granules or whole adrenal medullas were homogenized (10:1 V/W) in 1 M acetic acid, 20 mM HCl containing 1µg/ml PMSF and pepstatin. The procedures for extraction, Sephadex column elution and trypsin digestion have been described [Lewis, R. V. et al., Proc. Nat'l. Acad. Sci., U.S.A. 75, & 021 (1978)]. The radioreceptor assay employed neuroblastoma x glioma hybrid cells [Gerber, L. D. et al., Brain Res. 1515, 117 (1978)] with $^3$H-Leuenkephalin as the competing ligand. Radioimmunoassays were performed using a C-terminal directed Leu-enkephalin antibody and a N-terminal directed Met-enkephalin antibody. The characteristics of these antibodies have been described previously [Lewis. R. V., et al. Biochem. Biophys. Res. Commun. 89, 822 (1979)].

Reverse-phase high performance liquid chromatography was carried out using Lichrosorb RP-18 (EM-Hibar II) and Sepherisorb CN-propyl (LDC) with 5 µm resins in 4.6×250 mm columns. Formic acid (0.5 M) + pyridine (to pH 3 or pH 4) buffers were used with gradients of 1-propanol to elute the peptides and proteins [Lewis, R. V. et al., Int'l. J. Peptide Protein Res. 13, 493 (1979)]. All solvents were distilled over ninhydrin prior to use. An automated fluorescent peptide analyzer was used to monitor column effluents [Bohlen, P. et al., Anal. Biochem. 67, 437 (1975)].

Chromatography of extracts of whole bovine adrenal medulla (6.35 g) on Sephadex G-100 (5×100 cm) gave five peaks of radioreceptor active material. These correspond in molecular weight to approximately 20-24,000 (I); 10-15,000 (II); 7-10,000 (III); 3-5,000 (IV) and <1,000 (V). The receptor activity eluting in the regions of peaks I and II was detectable only when the material was digested with trypsin prior to assay. In addition, peaks III and IV activities were greatly increased after trypsin treatment. Extracts from chromaffin cells grown in primary culture showed the same pattern as the adrenal medulla when chromatographed on Sephadex G-75.

Chromaffin granules from bovine adrenal medulla were also lysed and subjected to the same chromatography on Sephadex G-100. The same five peaks of activity were again observed. Opioid activity was quantitatively determined by the radioreceptor assay before and after trypsin digestion of each of the pooled fractions from the whole medulla and granules. The results (Table I) show that the amounts of activity in peaks II, III, and IV relative to each other are similar from both sources. The amount of peak I relative to the other peaks was found to be more than 3-fold higher in the whole medulla than in the granules. This may indicate uptake of this largest peptide by the granules followed by proteolytic processing within the granules. Since peaks I, II, III and IV all showed considerably greater activity in the radioreceptor assay when predigested with trypsin, active peptide sequence must be contained within a larger peptide.

TABLE I

| Peak | Radioreceptor Assay of Peaks From Sephadex G-100 | |
|---|---|---|
| | Trypsin Digested | Native |
| | Adrenal Medulla[1] | |
| I | 6.9 | 0.6 |
| II | 12.5 | <0.05 |
| III | 10.9 | 1.9 |

TABLE I-continued

| Peak | Radioreceptor Assay of Peaks From Sephadex G-100 | |
|---|---|---|
| | Trypsin Digested | Native |
| IV | 5.1 | 2.2 |
| V | 12.0 | 12.4 |
| | Chromaffin Granules[1] | |
| I | 0.8 | 0.2 |
| II | 4.7 | 0.7 |
| III | 4.4 | 2.4 |
| IV | 1.7 | 0.6 |
| V | 4.8 | 5.0 |

[1]These values are for 10 g wet weight of bovine adrenal medulla without correction for recovery and are expressed as nmoles/peak.

Aliquots of the five (G-100) peaks from granules and medulla were assayed with or without digestion with trypsin. Tryptic peptides derived from peaks (G-100) I-IV interacted well with the N-terminal specific antiserum and gave values of the same order as the radioreceptor assay. Digestion with trypsin also yielded peptides which were immunoreactive using C-terminal specific antibody. These results, that an immunoreactive peptide is significantly increased after trypsin digestion of peaks (G-100) I-IV, are in accord with those obtained with the radioreceptor assay. They indicate that an active peptide is released from a larger peptide by the trypsin digestion and that the larger peptides are not themselves active.

Peak IV from G-100 is further characterized by chromatography on an HPLC Lichrosorb RP-18 column (10 µm, 4.6×250 mm ) using a linear 0-20% 1-propanol gradient in 0.5 m formic acid - 0.4 m pyridine at pH approximately 4.0 and a flow rate of about 30 ml/hour. Aliquots of fractions were radioreceptor assayed with and without trypsin digestion. The results show a complex pattern of peptides with at least 6 peptides having opioid activity or having active tryptic peptides. Chromatography of Peak IV from G-100 using RP-18 or CN-propyl HPLC columns have revealed a more complex pattern of opioid peptides, all of which, except IV-B (See Table I), show much greater activity after trypsin digestion. Table I schematically shows the peptides present in peak IV from G-100 and their percentages of the total activity in peak IV.

TABLE Ia

| | | | | % of Total PEAK IV |
|---|---|---|---|---|
| G-100 PEAK IV RP-18 | IV-A RP-18 | IV-A-1 | | 5.8 |
| | | IV-A-2 | | 7.0 |
| | IV-B CN | IV-B-1 | | 3.3 |
| | | IV-B-2 | | 3.9 |
| | IV-C CN | IV-C | | 8.3 |
| | IV-D CN | IV-D-1 | | 24.6 |
| | | IV-D-2 | | 5.1 |
| | IV-E CN | IV-E-1 | | 19.6 |
| | | IV-E-2 | | 17.7 |
| | IV-F | IV-F | | 4.7 |

Peak IV from the G-100 was chromatographed on RP-18. The active peptides from that chromatography, IV-A to IV-F, were further resolved on RP-18 or CN-propyl (CN) columns. The amount of each of the ten peptides (from one isolation) was determined and the percentage of each in the original peak IV is shown.

Three of the peptides from peak IV of G-100 were purified, IV-D-1, IV-D-2 and IV-E-2 using RP-18 and CN-propyl columns. Their amino acid analyses are shown in Table III. The active tryptic peptide from IV-D-1 co-chromatographs with Met[5]-enkephalin. The amino acid analyses of IV-D-2 and IV-E-2 differ by two amino acids, Gly and Arg, and their active tryptic peptides appear to be the same.

Using the RP-18 column and 1-propanol gradients both peaks II and III from G-100 were purified. Their amino acid analyses are shown in Table III. The major striking features of these analyses are the extremely high proline content, high Glx content, and very high Leu to Ile ratio. The two major active tryptic fragments from peak II were also purified by HPLC and shown to have the amino acid compositions of Met[5]-enkephalin and Lys[6]-Met[5]-enkephalin. Tryptic peptide mapping by HPLC has shown that peak III is not a fragment of peak II but is a separate protein with little sequence homology to Peak II.

TABLE II

| Characterization of Purified Enkephalin Like Compounds | | | | | |
|---|---|---|---|---|---|
| | Peak II[1] | Peak III[1] | IV-D-1[2] | IV-D-2[2] | IV-E-2[2] |
| Asx | 13 | 5 | 2 | 2 | 2 |
| Thr | 10 | 8 | 0 | 1 | 1 |
| Ser | 11 | 8 | 0 | 1 | 1 |
| Glx | 29 | 13 | 6 | 6 | 6 |
| Pro | 15 | 15 | 1 | 4 | 4 |
| Gly | 15 | 4 | 5 | 5 | 4 |
| Ala | 11 | 7 | 1 | 0 | 0 |
| Val | 4 | 0 | 2 | 1 | 1 |
| Met | 6 | 1 | 3 | 2 | 2 |
| Ile | 1 | 0 | 0 | 0 | 0 |
| Leu | 28 | 18 | 3 | 3 | 3 |
| Tyr | 7 | 2 | 3 | 3 | 3 |
| Phe | 4 | 1 | 2 | 2 | 2 |
| His | 2 | 1 | 0 | 1 | 1 |
| Lys | 16 | 8 | 3 | 3 | 3 |
| Arg | 8 | 3 | 1 | 5 | 4 |
| Cys | 8 | 5 | 0 | 0 | 0 |
| Total | 188 | 94 | 32 | 39 | 38 |
| Tryptic peptide[3] | Met | Met | Met | Met | Met |

[3]Trypsin cleavage yields a Met-enkephalin containing peptide.

Peak V from G-100 was chromatographed on Lichrosorb RP-18 (10 μm, 4.6×250 mm) using a step gradient of 0% (5 min), 5% (5 min), 10% (25 min), 15% (30 min) and 40% (15 min) 1-propanol in 0.5 M formic acid - 0.4 M pyridine (pH 4.0) with a flow rate of 35 ml/hr. Aliquots (20 μl) of fractions (3 min) were assayed with the radioreceptor assay. Peak V (G-100) was composed of several peptides which were equally active with or without trypsin digestion. Chromatography on RP-18 revealed opioid activity in the calibrated Met- and Leu-enkephalin positions and also in two regions before the elution position of Met-enkephalin in fractions 6 and 7 and one region after the elution position of Leu-enkephalin (fraction 16). [A similar chromatographic pattern was obtained from bovine striatal extracts although the relative amounts of these additional peptides differed].

The peptide eluting in the Leu-enkephal in position was purified to homogeneity by further chromatography on RP-18. It was shown to have the amino acid composition Tyr [1], Gly [2], Phe [1], and Leu [1]. [This represents the first chemical characterization of pure Leu-enkephalin from a natural source].

In order to determine whether fractions 6,7, and 16 were indeed separate entities differing chromatographically from the enkephalins, these fractions were lyophilized, redissolved and rechromatographed. Each opioid peptide eluted at its original position. These three fractions (6,7, and 16) were characterized by comparing their activity in the radioreceptor assay and the N- and C-terminal directed enkephalin radioimmunoassays (as shown in Table II). All the fractions interacted well with the N-terminal specific antiserum. None of the three fractions interacted very well with the C-terminal directed antiserum.

TABLE III

| Radioreceptor Assay and Radioimmunoassay of Fractions 6,7 and 16 from RP-18 | | | |
|---|---|---|---|
| Fraction | Radioreceptor | N-Terminal | C-Terminal |
| 6 | 1.1 | 0.8 | <0.01 |
| 7 | 1.4 | 1.2 | 0.03 |
| 16 | 1.3 | 1.2 | 0.06 |
| Met-enk (std) | 1.0 | 1.0 | 0.03 |
| Leu-enk (std) | 1.0 | 0.4 | 1.0 |

[1]These values are for 1.3 g wet weight of chromaffin granules isolated from 30 g of adrenal medulla and are expressed in nmoles/fraction.

Fraction 16 from peak V has been purified by isocratic elution from RP-18. Its amino acid composition was found to be Tyr (1), Gly (2), Phe (2), Met (1), Arg (1). When the peptide was digested with trypsin the active fragment coeluted with Arg[6]-Met enkephalin indicating this peptide has a C-terminal of Arg-Phe, giving the structure: Tyr-Gly-Gly-Phe-Met-Arg-Phe.

BIOLOGICAL ACTIVITY

Tyr-Gly-Gly-Phe-Met-Arg-Phe was prepared as follows:

2 g (1.0 mM) of tert-butyloxycarbonyl [BOC]-Phe Resin was prepared from chloromethylpolystyrene and Boc-Phe by the art recognized cesium salt method. To the Boc-Phe Resin was coupled 1.4 g of Amyloxycarbonyl [AOC]- Arg(TOS), 0.75 g of Boc-Met, 0.8 g Boc-Phe, 0.53 g Boc-Gly in two couplings, and 1.5 g of Boc-Tyr-p-bromo-benzyloxycarbonyl. The sequence of steps in each cycle was washed three times with methylene chloride (MC); 40% Trifluoroacetic acid/MC (consisting of a one minute prewash and a 20 minute deptotection step); a wash with MC; a wash with ethanol, wash three times with MC; and 2 minutes wash with a ten minute neutralization time with 10% triethylamine; followed by three washed MC. The Boc-amino acid and dicyclohexylcarbodimide were added in MC and stirred for two hours. If the resin showed complete coupling by the Kaiser test, the next cycle was begun. After the last addition, the resulting peptide-resin was washed with MC and ethanol after deprotection and dried. The peptide was resin by treatment with hydrogen fluoride for one hour at 0° C. Dimethylsulfide (0.5 ml) and anisole (6 ml) were added for protection. After evacuation, the peptide was washed with ether, dissolved in 20% acedic acid and lyophilized.

For the analgesic assay, mice were injected (intracerebral ventrical) with 6 n moles of the synthetic peptide. The tail flick response assay was carried out according to the method of Dayton, et al. Proc. Soc. Exp. Biol. Med. 142; 1011 (1973). The tail flick response (analgesic activity) was measured prior to injection and at 2, 5, and 10 minutes post injection time. Results are tabulated in Table IV.

TABLE IV

| No. of Mice Responsive/ Total No. of Mice | Injection Material | Dose | Volume | Prior Injection Time (Control) Predose | Post Injection Time 2 min. | 5 | 10 | 20 | Response |
|---|---|---|---|---|---|---|---|---|---|
| 0/3 | Saline | | 10 | 6.2 | 3.7 | — | 5.6 | — | Neg. |
| " | | | | 4.5 | 5.0 | | 5.8 | | Neg. |
| " | | | — | 5.0 | 4.3 | | 5.6 | | Neg. |
| " | Met Enk | 120 nm | 10nl. | 4.1 | 4.0 | | 6.3 | | Neg. |
| " | | | | 5.4 | 4.7. | | 5.9 | | Neg. |
| " | | | | 4.6 | 4.0 | | 5.0 | | Neg. |
| 3/3 | Acetylcholine | 20ng | 10nl | 4.6 | | 6.1 | >10 | | Pos. |
| " | | | | 5.0 | | >10 | | | Pos. |
| " | | | | 4.5 | | >10 | >10 | | Pos. |
| " | Beta-endorphin | 4.5nm | 5nl | 4.0 | 5.9 | >10 | | >10 | Pos. |
| " | | | | 4.7 | 3.0 | >10 | | >10 | Pos. |
| " | | | | 4.2 | 4.4 | >9 | | >10 | Pos. |
| 5/7 | | | | 5.4 | 3.8 | | | 8 | Neg. |
| " | | | | 4.4 | | 3.4 | >10 | | Pos. |
| " | | | | 4.0 | | 3.4 | 3.8 | | Neg. |
| " | | | | 4.3 | | 3.1 | | >10 | Pos. |
| 1/6 | Phosphate-Saline | | 10nl | 3.5 | | 4.5 | 4.4 | | Neg. |
| " | | | | 4.2 | 3.2 | | >10 | | Pos. |
| " | | | | 4.2 | | 3.5 | 3.9 | | Neg. |
| " | | | | 4.9 | | 6.0 | | 4.0 | Neg. |
| " | | | | 4.3 | 5.0 | 5.6 | | 8.0 | Neg. |
| " | | | | 4.2 | 5.5 | 4.8 | | 5.0 | Neg. |
| 4/8 | Arg$^6$-Phe$^7$ met-enkephalin | | 10nl | 5.7 | 4.9 | | 6.3 | | Neg. |
| " | | | | 5.2 | 4.6 | | 5.8 | | Neg. |
| " | | | 5nl | 4.6 | 4.3 | 5.4 | >10 | | Pos. |
| " | | | | 3.6 | 4.0 | 4.2 | >10 | | Pos. |
| " | | | | 3.7 | 3.4 | 3.8 | 5.0 | | Neg. |
| " | | | | 3.7 | 4.5 | 9.0 | >10 | | Pos. |
| " | | | | 4.0 | 4.0 | 4.0 | 4 | | Neg. |

DISCUSSION

All the results detailed here present further evidence that the enkephalins are formed via a biosynthetic pathway distinctly separate from that of $\beta$-endorphin, although they share a common amino terminal sequence. The enkephalin biosynthetic pathway has not been elucidated yet, but in the adrenal medullary chromaffin granules we have found a series of proteins that contain sequences which correspond to active opioid peptides. Proteins of 24,000, 18,000 and 9,500 M.W. were found as well as a number of peptides below 5,000 M.W. The proteins and peptides we have purified are all at present undergoing further chemical characterization to determine their interrelationships as well as their relationships to the enkephalins. In addition, several of the other peptides are nearly purified and will be characterized.

This demonstration by chemical methods that the enkephalins, as well as the enkephalin precursors, are localized in the chromaffin granules of the adrenal medulla is in accord with the immunocytochemical findings of Schultzberg et al. Acta Physiol. Scand., 103, 475. This strongly suggests that these precursors as well as the enkephalins are secreted into the blood stream during stimulation of the adrenal medulla. The enkephalins have a very short lifetime in serum and to be physiologically important they must interact with receptors in the adrenal gland itself. The other peptides present in the chromaffin granules may be more suited for transport to and effects in peripheral tissues. The physiological role of these peptides is certainly at present unknown but they may bear on some of the effects seen by the injection of various stable enkephalin analogs. It is interesting to speculate on the possibility that one or more of these peptides may emerge as a new class of neurohormone that is secreted in conjunction with the catecholamines.

The accessibility of the adrenal gland should allow the study of the biosynthesis of these peptides in vivo as well as factors that regulate the synthesis, storage and secretion of these new opioid peptides.

I claim:

1. The compound Tyr-Gly-Gly-Phe-Met-Arg-Phe essentially free of other endogenous peptides.

* * * * *